United States Patent [19]

Halasz et al.

[11] B 3,981,677

[45] Sept. 21, 1976

[54] OXIDATIVE HAIR DYE COMPOSITIONS CONTAINING N-SUBSTITUTED o-PHENYLENEDIAMINES AND METHOD FOR THEIR USE

[75] Inventors: Alexander Halasz, Norwalk, Conn.; Frederick Brody, deceased, late of Greenwich, Conn.; by Richard Newman, executor, New York, N.Y.

[73] Assignee: Clairol Incorporated, New York, N.Y.

[22] Filed: Jan. 2, 1974

[21] Appl. No.: 430,334

[44] Published under the second Trial Voluntary Protest Program on January 27, 1976 as document No. B 430,334.

[52] U.S. Cl. ..................................... 8/10.2; 8/10; 8/10.1; 8/11; 8/32; 260/573
[51] Int. Cl.² ..................................... A61K 7/13
[58] Field of Search .................... 8/10.2, 11, 32; 260/573

[56] References Cited
UNITED STATES PATENTS

| | | | |
|---|---|---|---|
| 923,635 | 6/1909 | Erdmann | 8/10.2 |
| 3,200,040 | 8/1965 | Lange | 8/10.2 X |
| 3,210,252 | 10/1965 | Blanke et al. | 8/10.2 |
| 3,236,891 | 2/1966 | Seemuller | 8/10.2 X |
| 3,337,411 | 8/1967 | Wilmsmann et al. | 8/10.2 |
| 3,415,608 | 12/1968 | Tucker | 8/10.2 |

FOREIGN PATENTS OR APPLICATIONS

| | | | |
|---|---|---|---|
| 518,199 | 2/1931 | Germany | 8/10.2 |

OTHER PUBLICATIONS

Heilingotter, Parfumerie Modern, vol. 48, (1955), pp. 55–60.

*Primary Examiner*—Stanley J. Friedman
*Assistant Examiner*—Vera C. Clarke
*Attorney, Agent, or Firm*—Irving Holtzman; George A. Mentis; David J. Mugford

[57] ABSTRACT

Hair dyeing compositions are disclosed which contain an N-substituted o-phenylenediamine, the N-substituent being an alkyl, alkoxyalkyl, hydroxyalkyl, alkylaminoalkyl, dialkylaminoalkyl, phenyl or substituted phenyl. These give reddish shades by purely oxidative means, and the shades are fast to wet treatments and are long-wearing. Also disclosed are methods of dyeing hair with these compositions, as well as certain novel compounds suitable for the purpose, e.g., N-(alkoxyalkyl)-o-phenylenediamines.

26 Claims, No Drawings

OXIDATIVE HAIR DYE COMPOSITIONS CONTAINING N-SUBSTITUTED O-PHENYLENEDIAMINES AND METHOD FOR THEIR USE

This invention relates to certain novel compositions for the dyeing of hair in reddish hues by oxidative means, comprising as a red-forming compound an N-substituted o-phenylenediamine. It further concerns a method of dyeing hair, and particularly living human hair, by the use of such compositions. The invention still further relates to certain novel N-substituted o-phenylenediamines which are useful in such compositions and methods.

The N-substituted o-phenylenediamines which are useful in the practice of this invention are designated by Formula I following:

(I) 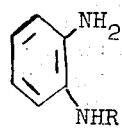

wherein R is alkyl of 1 to 4 carbon atoms; alkoxyalkyl of formula —R′—OR″ in which R′ is a divalent alkylene radical having 2 to 4 carbons and R″ is alkyl having 1 to 4 carbons; hydroxyalkyl of 2 to 4 carbon atoms and containing 1 to 3 hydroxyl radicals, alkylaminoalkyl (1 to 4 carbons in the alkyl moieties); dialkylaminoalkyl (1 to 4 carbons in the alkyl moieties); or phenyl or substituted phenyl.

The most commonly used method for dyeing hair, particularly human hair, is oxidative dyeing in which a mixture of aromatic compounds, generally of the benzenoid series, containing a plurality of nuclear amino and hydroxy functions, and which are themselves colorless, are converted to a blend of colored compounds within the hair fibers by oxidative processes. The colorless aromatic compounds (hereinafter called "dye precursors" or "precursors"), in a suitable base formulation, are mixed with a hydrogen peroxide developer shortly before use. The colored compounds, or "dyes" are formed by the self-oxidation of a precursor, or by oxidative coupling between two or more of the precursors. The dye precursors diffuse easily into the hair fibers by virtue of their low molecular weight and water solubility. The colored products developed by oxidation, however, remain entrapped within the hair fibers by virtue of their larger molecular weight, insolubility in water, and absorptive affinity to the internal hair surface. This is the basis for the so-called "permanent" tints and toners which last essentially for the life of the hair on the head because the dyes are relatively unaffected by wet treatments, such as shampooing and perspiration, and inaccessible to attack by chemicals and light.

By such oxidative means it has been possible to prepare a variety of natural shades, ranging from light blonde to dark brown. Thus far, however, it has not been possible to prepare shades of reddish hue by purely oxidative means, and with the advantages inherent therein. For the preparation of such shades, variously described as warm, red, reddish brown, auburn, titian, sandy, wine-colored, or burgundy, it has been necessary to incorporate in the oxidative mixture more or less of a reddish nitro dye of the nitro-phenylenediamine class, usually 2-nitro-p-phenylene-diamine, which is itself of reddish color, and neither formed nor altered by the oxidative medium. While this compound penetrates into the hair readily and dyes it, it does not have the permanence or wearing qualities of true oxidative colors, since because of its low molecular weight and water solubility it is gradually removed during several shampooings and other wet treatments. This leads to a gradual weakening and alternation of the shade away from the red.

It has now been found possible to dye hair in reddish hues by purely oxidative means, by including in the dyeing formulation an N-substituted o-phenylenediamine of Formula I. Under oxidative conditions this compound undergoes a self-coupling reaction, to give a reddish dye or dyes, which together with the dyes produced by the other precursors present, gives a composite hair color in the range of the warm colors, such as red, auburn, titian or the like. The shades are fast to shampooings and to wet treatments, and show excellent wearing qualities.

That the compound of Formula I contributes a red component to the shade can be demonstrated by applying it by itself, without the addition of other dye precursors. When mixed with alkaline peroxide and applied to gray hair, there is developed an orange to red hue which is fast to wet treatments such as repeated shampooings, or exposure to a simulated acid perspiration reagent for a length of time. It is thought that the self-oxidation of the N-substituted o-phenylenediamine of Formula I occurs to form a dihydrophenazine imine of Formula II according to the following scheme, although isomers and by-products are not excluded.

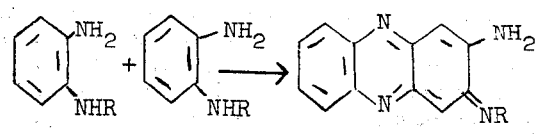

(II)

It is known to use o-phenylenediamine itself in oxidative dyeing compositions. However, this compound on self-oxidation gives a yellow product, and so cannot be used to form the reddish hues which are the subject of this invention.

The N-substituted o-phenylenediamines which are useful in this invention can be of a large variety as shown in Formula I. It is essential that the 4- and 5-positions of the benzene ring be unsubstituted, so that cyclization to the phenazine of Formula II be unimpeded. When R is alkyl, it can be methyl, ethyl, propyl, isobutyl, isopropyl, or the like, up to 4 carbon atoms. When R is alkoxyalkyl, it may be 2-methoxyethyl, 2-ethoxyethyl, 3-methoxypropyl, 4-methoxybutyl, 2-methoxypropyl, 3-methoxybutyl, and the like. When R is hydroxyalkyl it may be, for example, 2-hydroxyethyl, 3-hydroxypropyl, 2,3-dihydroxypropyl, or 2,3,4-trihydroxybutyl. When R is alkylaminoalkyl or dialkylaminoalkyl, it may be methylaminoethyl, ethylaminoethyl, 3-methylaminopropyl, 3-ethylaminopropyl, 2-dimethylaminoethyl, 3-dimethylaminopropyl, 2-diethylaminoethyl, 2-methylethylaminoethyl, 3-diethylaminopropyl, 3-dimethylamino-2-propyl, 4-dimethylaminobutyl, 3-dimethylaminobutyl or 3-dimethylaminoisobutyl. When R is substituted phenyl, the phenyl radical may be further substituted in any position by at least one substituent, which may be, for example, lower alkyl of 1 to 4 carbons, e.g., methyl, ethyl, n-propyl, isopropyl, butyl; halogeno, such as bromo, iodo or chloro; alkoxy e.g., methoxy and ethoxy, hydroxy; amino; lower alkyl-amino, lower dialkylamino, carboxy, carbamoyl, or sulfamoyl. The lower alkyl moieties in the aforesaid radicals will preferably contain 1 to 4 carbons.

The novel N-substituted o-phenylenediamines forming part of this invention are described by the following structure:

(III)

wherein $n$ is 2 to 4 and R' is lower alkyl having 1 to 4 carbons e.g., methyl, ethyl. These novel compounds may be prepared by methods previously known in the prior art, one excellent method being the reaction of o-nitrofluorobenzene with an amine of the structure $H_2N—(CH_2)_nOR'$, followed by reduction of the nitro group to amino.

In the practice of this invention a tinctorially effective amount of the N-substituted o-phenylenediamine (e.g. 0.02 to 5%) is incorporated in a hair dyeing composition. The quantity incorporated will depend upon the degree of redness desired in the shade on the head. Generally, 0.2 to 2% will be preferred for shades most commonly desired.

The N-substituted o-phenylenediamine will ordinarily be used in the composition together with other oxidation dye precursors in order to form a natural shade. Among the precursors which may be included are such well-known ingredients as p-phenylenediamine, p-toluenediamine, resorcinol, 2,4-diaminoanisole, o-phenylenediamine, o-aminophenol, p-aminophenol, m-aminophenol, hydroquinone, pyrogallol, 1-naphthol, 4-aminodiphenylamine, 4,4'-diaminodiphenylamine, and 3-methyl-5-pyrazolone. In such as blend a variety of oxidative reactions may occur on addition of peroxide mostly by oxidative coupling between two or more precursors of suitable structure. It is considered that besides that self-coupling of the N-substituted o-phenylenediamine it may also undergo oxidative coupling with one or more of the other precursors present. The final shade which is determined by trial is the shade desired.

When the dyeing is performed on hair other than white, the final shade is partly influenced by the color remaining on the substrate hair, whether from natural pigment, bleached pigment or previous dyes present. Since a portion of the original hair color is destroyed by the peroxide used in the dyeing application, the final shade after dyeing is influenced by the ratio of dye precursors to peroxide used.

Besides the oxidative dye precursors present in the formulation, it is also possible to have present some direct dyes, which are preformed dyes not requiring oxidation to develop their color. These are generally nitro dyes of yellow to reddish shade. Among yellow dyes which may be included are 4-nitro-o-phenylenediamine, 4-nitro-2-aminophenol, 5-nitro-2-aminophenol, and 2-nitro-4-aminophenol. Among reddish dyes may be mentioned principally 2-nitro-p-phenylenediamine. When the latter dye is used together with the dyes of this invention, each contributes a share of redness to the final shade. The final shade then has a greater fastness to wet treatments than conventional shades using 2-nitro-p-phenylenediamine as the sole source of redness. When used, 2-nitro-p-phenylenediamine may be added in an amount ranging from 0.01 to 2% by weight of the composition, though 0.01 to 0.5% is preferred and gives shades up to the reddest most commonly desired.

In addition to hair coloring ingredients, the compositions of this invention may contain one or more dyeing assistants and adjuvants commonly used in oxidative dyeing, such as surface active agents, alkalizing agents, buffers, solvents, thickening agents, antioxidants, sequestering agents, conditioning agents, and perfumes.

Surface active agents which may be used may be anionic, non-ionic or cationic. Illustrative of surfactants there can be mentioned: sodium palmitate, sodium oleate, ammonium oleate, sodium lauryl sulfate, sodium myristyl sulfate, sodium polyoxyethylene lauryl sulfate, glyceryl monostearate, sodium palmitic methyl taurate, cetyl pyridinium chloride, lauric diethanolamide, polyoxyethylene stearate, stearyl dimethyl benzyl ammonium chloride, sodium dodecylbenzene sulfonate, sodium nonylnaphthalenesulfonate, sodium N-methyl-N-oleoyl taurate, oleic acid ester of sodium isethionate, and the like.

As alkalizing agents there may be used preferably ammonia, but also sodium hydroxide, sodium phosphate, sodium carbonate, monoethanolamine, diethanolamine, and others. The amount of alkalizing agent used is sufficient to give a pH in the range of 8 to 12.

As buffering agents there may be used various ammonium salts, such as ammonium acetate, ammonium citrate, ammonium tartrate, and ammonium soaps such as ammonium palmitate, oleate, and linoleate.

As thickening agents there may be used, besides those surfactants which in themselves perform a thickening function, vegetable gums such as agar, cellulose derivatives such as sodium carboxymethyl cellulose, hydroxyethyl cellulose and others.

As antioxidant stabilizers there may be used sodium sulfite, thioglycollic acid, ascorbic acid, and others.

As sequestering agents there may be used the sodium salt of ethylenediamine tetraacetic acid and similar compounds.

As organic solvents there may be used ethanol, isopropyl alcohol, ethylene glycol, propylene glycol, glycerine, and others.

The compositions of this invention generally contain water, and the amount can vary from about 5 to 99% depending on the physical form of the composition, whether paste, slurry, thin liquid, or foam.

The dyeing compositions of this invention are applied to the human head by methods conventional for oxidation dyeing. Just before use they are mixed with a suitable volume of hydrogen peroxide, either as an aqueous solution, or as a creme emulsion containing the peroxide, using amounts necessary to give preferably a 3% concentration of hydrogen peroxide in the total mixture. Alternatively, a solid or crystalline peroxide may be added, such as urea peroxide, melamine peroxide, or the like. Further optionally, an oxidizing agent other than a peroxide may be added, such as sodium perborate.

The mixture is applied either to the whole head by the shampoo-in method, or first to the roots by means of a brush, swab, or spatula, and when dyeing of the roots is complete, combed through the rest of the hair to complete the application. The head is then shampooed and rinsed. In an alternative application method, the dyeing composition and a hydrogen peroxide solution are packaged in separate chambers of a two-compartment aerosol container; a propellant fluid is in the same chamber as the dyes. The dyeing composition and peroxide become mixed upon release of the aerosol valve, and the mixture is applied to the head as a foam. In general, the dye composition will be in contact with the hair for a time period ranging from 10–60 minutes and at a temperature in the range of from about 25°C to 40°C.

The following Examples illustrate the various aspects of the present invention. It is to be understood, however, that the invention is not limited thereto.

EXAMPLE 1

Preparation of N-(2-methoxyethyl)-o-phenylenediamine

To a mixture of 70.5 g. (0.5 mole) o-fluoronitrobenzene, 26 g. (0.25 mole) sodium carbonate, and 200 ml. ethanol heated at reflux temperature was added dropwise 41 g. (0.55 mole) 2-methoxyethylamine. The mixture was then heated at the boil under reflux for 12 hours, allowed to cool and stand at room temperature overnight, and then clarified by filtration for removal of inorganic salts. From the clear solution, by evaporation to dryness, was obtained 100 g., an almost quantitative yield, of N-(2-methoxyethyl)-2-nitroaniline, m.p. 30°–35°, in essentially pure form, as shown by its elementary analysis in percent: Calculated for $C_9H_{12}N_2O_3$: C, 55.1; H, 6.12; N, 14.3; found: C, 54.6; H, 5.99; N, 13.8.

The nitroaniline, 19.6 g. was reduced by hydrogen in 100 ml. ethanol, using 1 g. palladium-on-charcoal as catalyst. The uptake of hydrogen was complete in 20 minutes, whereupon the catalyst was filtered off and the solvent removed. The residue, which was a liquid at this stage, was converted to the hydrochloride, a hygroscopic salt of m.p. 137°–144°. This was the hydrochloride of N-(2-methoxyethyl)-o-phenylenediamine.

EXAMPLE 2

Dyeing with N-methyl-o-phenylenediamine

The composition:
1.0 g. N-methyl-o-phenylenediamine
10 ml. ethanol
1 g. Carbopol 934
0.01 g. sodium lauryl sulfate
3.8 g. ammonium acetate
15 ml. 28% ammonia
made up to 100 ml. with water
was mixed with 100 ml. 6% hydrogen peroxide. A sample of gray hair was immersed in the mixture and allowed to remain in it for 20 minutes at 30°C, after which it was removed, shampooed and rinsed. The hair was dyed an orange shade which was fast to shampooing and to acid perspiration.

EXAMPLES 3–8

Dyeing with various o-phenylenediamines

The following Examples are given in tabular form. The procedure of Example 2 was used except that the N-substitued o-phenylenediamine of the particular example was substituted for the N-methyl-o-phenylenediamine of Example 2. The shade obtained on gray hair is given for each dyeing. All of the dyeings were very fast to wet treatments, including repeated shampooings and acid perspiration. The N-substituted o-phenylenediamine employed in the respective examples is given by the formula:

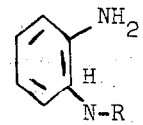

the value of R for the particular N-substituted o-phenylenediamine used in the particular example being given in Column 2.

| Example No. | R | Shade on Gray Hair |
|---|---|---|
| 3 | Isopropyl | Orange |
| 4 | 2-hydroxyethyl | Strong orange |
| 5 | 2-methoxyethyl | Orange |
| 6 | Phenyl | Red |
| 7 | p-hydroxyphenyl | Dull red |
| 8 | 3-dimethylaminopropyl | Orange |

EXAMPLE 9

Dyeing with N-2-hydroxyethyl)-o-phenylenediamine in Oleate Base

The composition:
1 g. N-(2-hydroxyethyl)-o-phenylenediamine
15 ml. ethanol
1 g. sodium lauryl sulfate
3 g. diethyleneglycol monoethyl ether
21 g. oleic acid
4 g. glycerine
9 g. propylene glycol
10 g. 28% ammonium
made up to 100 ml. with water
was mixed with 100 ml. 6% hydrogen peroxide. In the mixture was immersed a sample of gray hair, which was left in contact with the mixture for 30 minutes at 30°C, then removed, shampooed and rinsed. The hair was dyed a beautiful orange shade which was very fast to several sequential shampooings and exposure to acid perspiration.

EXAMPLES 10–12

Dyeing with various o-phenylenediamines in Oleate Base

The following Examples are given in tabular form. The procedure of Example 9 was followed, except that in place of N-(2-hydroxyethyl)-o-phenylenediamine there was used an equal weight of another N-substituted o-phenylenediamine, as named in the Table below. The shade on gray hair is shown in the Table. The dyeings were fast to repeated shampooings and to exposure to acid perspiration.

| Example No. | N-substituted o-phenylenediamine used | Shade on Gray Hair |
|---|---|---|
| 10 | 2-aminodiphenylamine | Red |
| 11 | 4'-carboxy-2-aminodiphenylamine | Rose |
| 12 | 4'-hydroxy-2-aminodi- | |

| Example No. | N-substituted o-phenylenediamine used | Shade on Gray Hair |
|---|---|---|
| | phenylamine | Dull orange |

EXAMPLE 13

Natural shade using N-(2-hydroxyethyl)-o-phenylenediamine

A. The following composition was prepared:
0.75 g. N-(2-hydroxyethyl)-o-phenylenediamine
0.50 g. p-aminophenol
0.50 g. 2,4-diaminoanisole sulfate
10 ml. ethanol
1 g. Carbopol 934
0.01 g. sodium lauryl sulfate
3.8 g. ammonium acetate
15 ml. 28% ammonia
Made up to 100 ml.

The composition was mixed with 100 ml. 6% hydrogen peroxide, and the mixture poured on a sample of gray hair, and allowed to remain in contact with the hair for 20 minutes at 30°C. The hair was removed, shampooed and rinsed. It was dyed a soft medium burgundy shade with pronounced red highlights, which was fast to several shampooings and to treatment with acid perspiration.

B. A similar shade was prepared using a conventional oxidation dye blend, i.e., one not containing an N-substituted o-phenylenediamine. The composition of the conventional shade formulation was as follows:
0.075 g. m-aminophenol
0.11 g. 2,4-diaminoanisole sulfate
0.2 g. p-toluenediamine sulfate
1.28 g. 2-nitro-p-phenylenediamine
0.075 g. resorcinol
0.050 g. hydroquinone
21 g. oleic acid
4 g. glycerine
3 g. diethyleneglycol monoethyl ether
9 g. propylene glycol
10 g. isopropanol
1 g. sodium lauryl sulfate
10 g. 28% ammonia
made up to 100 ml. with water When this was dyed on gray hair in the same manner as the novel composition above, it gave a similar burgundy shade with red highlights. However, the hair so dyed on successive shampooings gradually became weaker and drabber in shade, losing its redness. On exposure to standard acid perspiration solution over night the shade lost considerable strength and redness.

EXAMPLE 14

Natural shade using N-(2-hydroxyethyl)-o-phenylenediamine

A. The following composition was prepared:
0.25 g. N-(2-hydroxyethyl)-o-phenylenediamine
0.066 g. N,N-bis(2-hydroxyethyl)-p-phenylenediamine hydrochloride
0.070 g. 1-m-aminophenyl-3-methyl-5-pyrazolone
15 ml. ethanol
1 g. sodium lauryl sulfate
3 g. diethyleneglycol monoethyl ether
21 g. oleic acid
4 g. glycerine
9 g. propylene glycol
10 g. 28% ammonia
Water to 100 ml.

The composition was mixed with 100 ml. 6% hydrogen peroxide, the mixture poured on a sample of gray hair, and allowed to remain in contact with the hair for 30 minutes at 30°C. The hair sample was removed, shampooed and rinsed. It was dyed a warm auburn brown shade, fast to successive shampooings and to treatment with a synthetic acid perspiration solution.

B. A similar shade was prepared using conventional oxidation dye components, not including an N-substituted o-phenylenediamine. That is, in place of the dye components (first three ingredients) of the above composition, there were used the following dye components, the remaining ingredients of that composition being the same:
0.063 g. m-aminophenol
0.016 g. 4-nitro-o-phenylenediamine
0.105 g. 2,4-diaminoanisole sulfate
0.025 g. 4-amino-2-nitrophenol
0.47 g. toluene-2,5-diamine
0.47 g. 2-nitro-p-phenylenediamine
0.31 g. resorcinol
0.07 g. o-aminophenol
0.035 g. hydroquinone When the formulation containing conventional dye components was dyed on gray hair, it gave an auburn brown shade which, however, was not fast to wet treatments. It lost strength and warmth both in repeated shampoos and in exposure to acid perspiration, becoming weak, dull and "mousy" looking.

EXAMPLE 15

N-substituted o-phenylenediamine combined with a conventional red dye

The following composition was prepared:
0.070 g. p-phenylenediamine
0.070 g. resorcinol
1.25 g. N-(2-hydroxyethyl)-o-phenylenediamine
0.075 g. 2-nitro-p-phenylenediamine
0.014 g. 4-nitro-o-phenylenediamine
15 ml. isopropanol
1 g. sodium lauryl sulfate
3 g. diethyleneglycol monoethyl ether
21 g. oleic acid
4 g. glycerine
9 g. propylene glycol
10 g. 28% ammonia
water to make 100 ml.

When this was mixed with peroxide and the mixture applied to gray hair as in the previous Examples, the hair was dyed an attractive light auburn shade which was faster to wet treatments than a similar shade made without the use of an N-substituted o-phenylenediamine.

EXAMPLE 16

N-substituted o-phenylenediamine combined with a conventional red dye

The following composition was prepared:
0.04 g. p-phenylenediamine
0.04 g. resorcinol
0.5 g N-(2-hydroxyethyl)-o-phenylenediamine
0.027 g. 2-nitro-p-phenylenediamine
1.5 g. Carbopol 934

7.5 g. ammonium acetate
10 ml. 28% ammonia
1.0 g. sodium lauryl glycol ether sulfate
water to make 100 ml.

When this composition mixed with peroxide was applied to gray hair as in the previous Examples, it gave a beautiful muted auburn shade which was faster to wet treatments than a similar shade prepared without the use of an N-substituted o-phenylenediamine.

What is claimed is:

1. An oxidation hair dyeing composition comprising a water containing hair dye carrier and a tinctorially effective amount of an o-phenylenediamine of the formula:

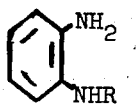

wherein R is alkyl having 1 to 4 carbon atoms.

2. A composition according to claim 1 containing 0.02 to 5% of said o-phenylenediamine.

3. A composition according to claim 2 also including p-phenylenediamine and resorcinol.

4. A composition according to claim 2 also including p-toluenediamine and resorcinol.

5. A composition according to claim 2 also including 2-nitro-p-phenylenediamine.

6. An oxidation hair dyeing composition comprising a water containing hair dye carrier and a tinctorially effective amount of an o-phenylenediamine of the formula:

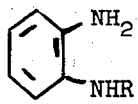

wherein R is hydroxyalkyl having 2 to 4 carbon atoms and 1 to 3 hydroxy groups.

7. A composition according to claim 6 containing 0.02 to 5% by weight of said o-phenylenediamine.

8. A composition according to claim 7 also including p-phenylenediamine and resorcinol.

9. A composition according to claim 7 also including p-toluenediamine and resorcinol.

10. A composition according to claim 7 also including 2-nitro-p-phenylenediamine 11. An oxidation hair dyeing composition comprising a water containing hair dye carrier and a tinctorially effective amount of an o-phenylenediamine of the formula:

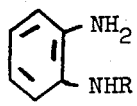

wherein R is alkoxyalkyl in which the alkyl moiety in each instance has 1 to 4 carbon atoms.

12. An oxidation hair dyeing composition comprising a water containing hair dye carrier and a tinctorially effective amount of an o-phenylenediamine of the formula:

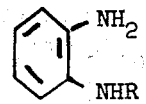

wherein R is dialkylaminoalkyl in which the alkyl moiety in each instance has from 1 to 4 carbon atoms.

13. An oxidation hair dyeing composition comprising a water containing hair dye carrier and a tinctorially effective amount of an o-phenylenediamine of the formula:

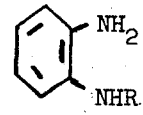

wherein R is phenyl.

14. A composition according to claim 11 containing 0.02 to 5% by weight of said o-phenylenediamine.

15. A composition according to claim 14 also including p-phenylenediamine and resorcinol.

16. A composition according to claim 14 also including p-toluenediamine and resorcinol.

17. A composition according to claim 14 also including 2-nitro-p-phenylenediamine.

18. An oxidation hair dyeing composition comprising a water containing hair dye carrier and a tinctorially effective amount of an o-phenylenediamine of the formula:

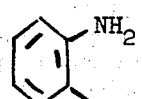

wherein R is alkoxy (C1–C4) phenyl.

19. An oxidation hair dyeing composition comprising a water containing hair dye carrier and a tinctorially effective amount of an o-phenylenediamine of the formula:

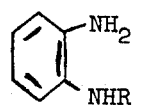

wherein R is alkyl (C1–C4) phenyl.

20. An oxidation hair dyeing composition comprising a water containing hair dye carrier and a tinctorially effective amount of an o-phenylenediamine of the formula:

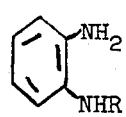

wherein R is halophenyl.

21. An oxidation hair dyeing composition comprising a water containing hair dye carrier and a tinctorially effective amount of an o-phenylenediamine of the formula:

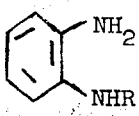

wherein R is aminophenyl.

22. An oxidation hair dyeign composition comprising a water containing hair dye carrier and a tinctorially effective amount of an o-phenylenediamine of the formula:

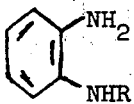

wherein R is hydroxphenyl.

23. An oxidation hair dyeing composition comprising a water containing hair dye carrier and a tinctorially effective amount of an o-phenylenediamine of the formula:

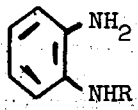

wherein R is carboxyphenyl.

24. A method of dyeing hair which comprises applying thereto an effective amount of a composition comprising hydrogen peroxide, a water containing hair dye carrier and 0.02 to 5% by weight based on the total weight of said composition of an o-phenylenediamine of the formula:

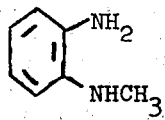

and then removing said composition from said hair.

25. A method of dyeing hair which comprises applying thereto an effective amount of a composition comprising hydrogen peroxide, a water containing hair dye carrier and 0.02 to 5% by weight based on the total weight of said composition of an o-phenylenediamine of the formula:

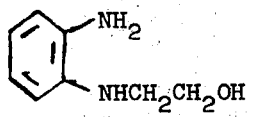

and then removing said composition from said hair.

26. A method of dyeing hair which comprises applying thereto an effective amount of a composition comprising hydrogen peroxide, a water containing hair dye carrier and 0.02 to 5% by weight based on the total weight of said composition of an o-phenylenediamine of the formula:

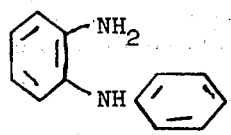

and then removing said composition from said hair.

* * * * *